(12) United States Patent
Fournie et al.

(10) Patent No.: US 8,361,024 B2
(45) Date of Patent: *Jan. 29, 2013

(54) ADMINISTRATION FEEDING SET

(75) Inventors: Glenn G. Fournie, Smithton, IL (US);
James M. Harr, Foristell, MO (US);
Kevin C. Meier, St. Louis, MO (US);
Ricky A. Sisk, Washington, MO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,087

(22) Filed: Sep. 26, 2011

(65) Prior Publication Data

US 2012/0078196 A1 Mar. 29, 2012

Related U.S. Application Data

(60) Continuation of application No. 12/795,889, filed on Jun. 8, 2010, now Pat. No. 8,034,028, which is a continuation of application No. 11/678,350, filed on Feb. 23, 2007, now Pat. No. 7,753,881, which is a division of application No. 10/853,958, filed on May 25, 2004, now Pat. No. 7,462,170.

(51) Int. Cl.
*A61M 37/00* (2006.01)
(52) U.S. Cl. .................. 604/131; 604/151; 604/246
(58) Field of Classification Search .................. 604/131, 604/65, 151, 246, 248
See application file for complete search history.

(56) References Cited

U.S. PATENT DOCUMENTS

| | | | |
|---|---|---|---|
| 3,626,938 A | 12/1971 | Versaci | |
| 3,896,803 A | 7/1975 | Mason | |
| 3,985,133 A | 10/1976 | Jenkins et al. | |
| 4,396,385 A | 8/1983 | Kelly et al. | |
| 4,460,355 A | 7/1984 | Layman | |
| 4,460,366 A | 7/1984 | Shinno | |
| 4,519,792 A | 5/1985 | Dawe | |
| 4,557,725 A | 12/1985 | Heyne et al. | |
| 4,604,093 A | 8/1986 | Brown et al. | |
| 4,605,396 A | 8/1986 | Tseo et al. | |
| 4,685,910 A | 8/1987 | Schweizer | |
| D293,129 S | 12/1987 | Millerd et al. | |
| 4,710,166 A | 12/1987 | Thompson et al. | |
| 4,714,463 A | 12/1987 | Archibald et al. | |
| 4,741,736 A | 5/1988 | Brown | |
| 4,789,000 A | 12/1988 | Aslanian | |
| 4,798,590 A | 1/1989 | O'Leary et al. | |
| 4,820,268 A | 4/1989 | Kawamura et al. | |
| 4,831,866 A | 5/1989 | Forkert et al. | |
| 4,838,856 A | 6/1989 | Mulreany et al. | |
| 4,840,542 A | 6/1989 | Abbott | |

(Continued)

FOREIGN PATENT DOCUMENTS

DE 4020522 A1 1/1992
EP 0398583 A2 11/1990

(Continued)

OTHER PUBLICATIONS

European Exam Report regarding related application serial No. EP 05753418.2 dated Jun. 25, 2010, 5 pgs.

(Continued)

*Primary Examiner* — Theodore Stigell

(57) ABSTRACT

An administration feeding set for use with a flow control apparatus to deliver fluid from at least one fluid source to a patient. The set includes tubing for flow of fluid along a fluid pathway and a mounting member on the tubing adapted to engage the flow control apparatus. The mounting member has at least two receiving portions co-axial with the fluid pathway. The set also includes one or more identification members selectively positioned on one or more of the at least two receiving portions of the mounting member to permit identification of the administration feeding set as having a particular functional configuration different from another functional configuration.

16 Claims, 13 Drawing Sheets

U.S. PATENT DOCUMENTS

| | | | |
|---|---|---|---|
| 4,845,487 A | 7/1989 | Frantz et al. | |
| 4,850,805 A | 7/1989 | Madsen et al. | |
| 4,850,980 A | 7/1989 | Lentz et al. | |
| 4,884,103 A | 11/1989 | Yamada | |
| 4,898,581 A | 2/1990 | Iwatschenko | |
| 4,913,703 A * | 4/1990 | Pasqualucci et al. | 604/153 |
| 4,915,688 A | 4/1990 | Bischof et al. | |
| 4,918,973 A | 4/1990 | Kruse | |
| 4,919,596 A | 4/1990 | Slate et al. | |
| 4,950,254 A | 8/1990 | Andersen et al. | |
| 4,955,860 A | 9/1990 | Ruano | |
| 5,057,081 A | 10/1991 | Sunderland | |
| 5,084,031 A | 1/1992 | Todd et al. | |
| 5,111,683 A | 5/1992 | Fond | |
| 5,147,313 A | 9/1992 | Dikeman | |
| 5,158,437 A | 10/1992 | Natwick et al. | |
| 5,171,029 A | 12/1992 | Maxwell et al. | |
| 5,181,910 A | 1/1993 | Scanlon | |
| 5,197,322 A | 3/1993 | Indravudh | |
| 5,201,711 A | 4/1993 | Pasqualucci et al. | |
| 5,213,483 A | 5/1993 | Flaherty et al. | |
| 5,244,463 A | 9/1993 | Cordner, Jr. et al. | |
| 5,253,640 A | 10/1993 | Falb et al. | |
| 5,272,917 A | 12/1993 | Pippert | |
| 5,299,446 A | 4/1994 | Pardinas et al. | |
| 5,318,413 A | 6/1994 | Bertoncini | |
| 5,364,364 A | 11/1994 | Kasvikis et al. | |
| 5,368,562 A | 11/1994 | Blomquist et al. | |
| 5,374,248 A | 12/1994 | Lopez | |
| 5,374,251 A | 12/1994 | Smith | |
| 5,415,641 A | 5/1995 | Yerlikaya et al. | |
| 5,431,627 A | 7/1995 | Pastrone et al. | |
| 5,437,642 A | 8/1995 | Thill et al. | |
| 5,439,452 A | 8/1995 | McCarty | |
| 5,443,543 A | 8/1995 | Epes et al. | |
| 5,499,968 A | 3/1996 | Milijasevic et al. | |
| 5,531,680 A | 7/1996 | Dumas et al. | |
| 5,531,697 A | 7/1996 | Olsen et al. | |
| 5,562,615 A | 10/1996 | Nassif | |
| 5,569,026 A | 10/1996 | Novak | |
| 5,584,671 A | 12/1996 | Schweitzer, Jr. et al. | |
| 5,589,026 A | 12/1996 | Perecman | |
| 5,603,353 A | 2/1997 | Clark et al. | |
| 5,634,907 A | 6/1997 | Rani et al. | |
| 5,681,294 A | 10/1997 | Osborne et al. | |
| 5,704,584 A | 1/1998 | Winterer et al. | |
| 5,755,683 A | 5/1998 | Houle et al. | |
| 5,772,637 A | 6/1998 | Heinzmann et al. | |
| 5,807,321 A | 9/1998 | Stoker et al. | |
| 5,807,333 A | 9/1998 | Osborne et al. | |
| 5,814,015 A | 9/1998 | Gargano et al. | |
| 5,840,058 A | 11/1998 | Ammann et al. | |
| 5,951,510 A | 9/1999 | Barak | |
| 6,042,564 A | 3/2000 | Barak | |
| 6,059,544 A | 5/2000 | Jung et al. | |
| 6,117,115 A | 9/2000 | Hill et al. | |
| 6,139,748 A | 10/2000 | Ericson et al. | |
| 6,142,979 A | 11/2000 | McNally et al. | |
| 6,164,921 A | 12/2000 | Moubayed et al. | |
| 6,250,130 B1 | 6/2001 | Howard et al. | |
| 6,280,440 B1 | 8/2001 | Gocho | |
| 6,283,719 B1 | 9/2001 | Frantz et al. | |
| 6,364,857 B1 | 4/2002 | Gray et al. | |
| 6,368,314 B1 | 4/2002 | Kipfer et al. | |
| 6,422,057 B1 | 7/2002 | Anderson | |
| 6,475,180 B2 | 11/2002 | Peterson et al. | |
| 6,491,659 B1 | 12/2002 | Miyamoto | |
| 6,530,907 B1 | 3/2003 | Sugahara et al. | |
| 6,582,387 B2 | 6/2003 | Derek et al. | |
| 6,626,862 B1 | 9/2003 | Duchon et al. | |
| 6,638,263 B1 | 10/2003 | Theeuwes et al. | |
| 6,641,562 B1 | 11/2003 | Peterson | |
| 6,659,976 B2 | 12/2003 | Beck et al. | |
| 6,666,821 B2 | 12/2003 | Keimel | |
| 6,880,808 B2 | 4/2005 | McPeak et al. | |
| 6,942,636 B2 | 9/2005 | Holst et al. | |
| 6,985,870 B2 | 1/2006 | Martucci et al. | |
| 7,092,797 B2 | 8/2006 | Gaines et al. | |
| 7,462,170 B2 * | 12/2008 | Fournie et al. | 604/248 |
| 7,469,716 B2 | 12/2008 | Parrino et al. | |
| 7,608,059 B2 * | 10/2009 | Harr et al. | 604/131 |
| 7,661,582 B2 | 2/2010 | Mollstam | |
| 7,753,881 B2 * | 7/2010 | Fournie et al. | 604/131 |
| 7,753,883 B2 * | 7/2010 | Fournie et al. | 604/131 |
| 8,034,028 B2 * | 10/2011 | Fournie et al. | 604/131 |
| 2002/0169424 A1 | 11/2002 | Miles et al. | |
| 2005/0278054 A1 | 12/2005 | Gaines et al. | |
| 2010/0249722 A1 | 9/2010 | Fournie et al. | |

FOREIGN PATENT DOCUMENTS

| | | |
|---|---|---|
| JP | 11-002358 A | 1/1999 |
| NL | 9500612 A | 11/1996 |
| WO | 9407556 A1 | 4/1994 |
| WO | 9720594 A1 | 6/1997 |
| WO | 03029706 A1 | 4/2003 |
| WO | 2004028595 A1 | 4/2004 |

OTHER PUBLICATIONS

European Search Report regarding related application serial No. EP 09173818.7 dated Jun. 28, 2010, 7 pgs.

European Search Report regarding related application serial No. EP 09173821.1 dated Jun. 28, 2010, 9 pgs.

European Search Report regarding related application serial No. EP 09173822.9 dated Jun. 28, 2010, 8 pgs.

Office action issued Jun. 14, 2007 in related U.S. Appl. No. 10/853,958; 7 pgs.

Response filed Aug. 28, 2007 to Office Action dated Jun. 14, 2007 from related U.S. Appl. No. 10/853,958; 11 pgs.

Office action issued Mar. 18, 2008 in related U.S. Appl. No. 10/853,958; 8 pgs.

Response filed May 16, 2008 to Office Action dated Mar. 18, 2008 from related U.S. Appl. No. 10/853,958; 13 pgs.

Office action issued Mar. 24, 2009 in related U.S. Appl. No. 11/961,158; 8 pgs.

Response filed Jul. 1, 2009 to Office Action dated Mar. 24, 2009 from related U.S. Appl. No. 11/961,158; 10 pgs.

Office action issued Oct. 21, 2009 in related U.S. Appl. No. 11/961,158; 8 pgs.

Response filed Jan. 26, 2010 to Office Action dated Oct. 21, 2009 from related U.S. Appl. No. 11/961,158; 11 pgs.

Office action issued Mar. 24, 2009 in related U.S. Appl. No. 11/678,350; 6 pgs.

Response filed Jul. 1, 2009 to Office Action dated Mar. 24, 2009 from related U.S. Appl. No. 11/678,350; 8 pgs.

Office action issued Oct. 26, 2009 in related U.S. Appl. No. 11/678,350; 8 pgs.

Response filed Jan. 26, 2010 to Office Action dated Oct. 26, 2009 from related U.S. Appl. No. 11/678,350; 9 pgs.

Office action issued Feb. 3, 2011 in related U.S. Appl. No. 12/795,889—7 pgs.

Response filed May 3, 2011 to Office Action dated Feb. 3, 2011 from related U.S. Appl. No. 12/795,899—3 pgs.

* cited by examiner

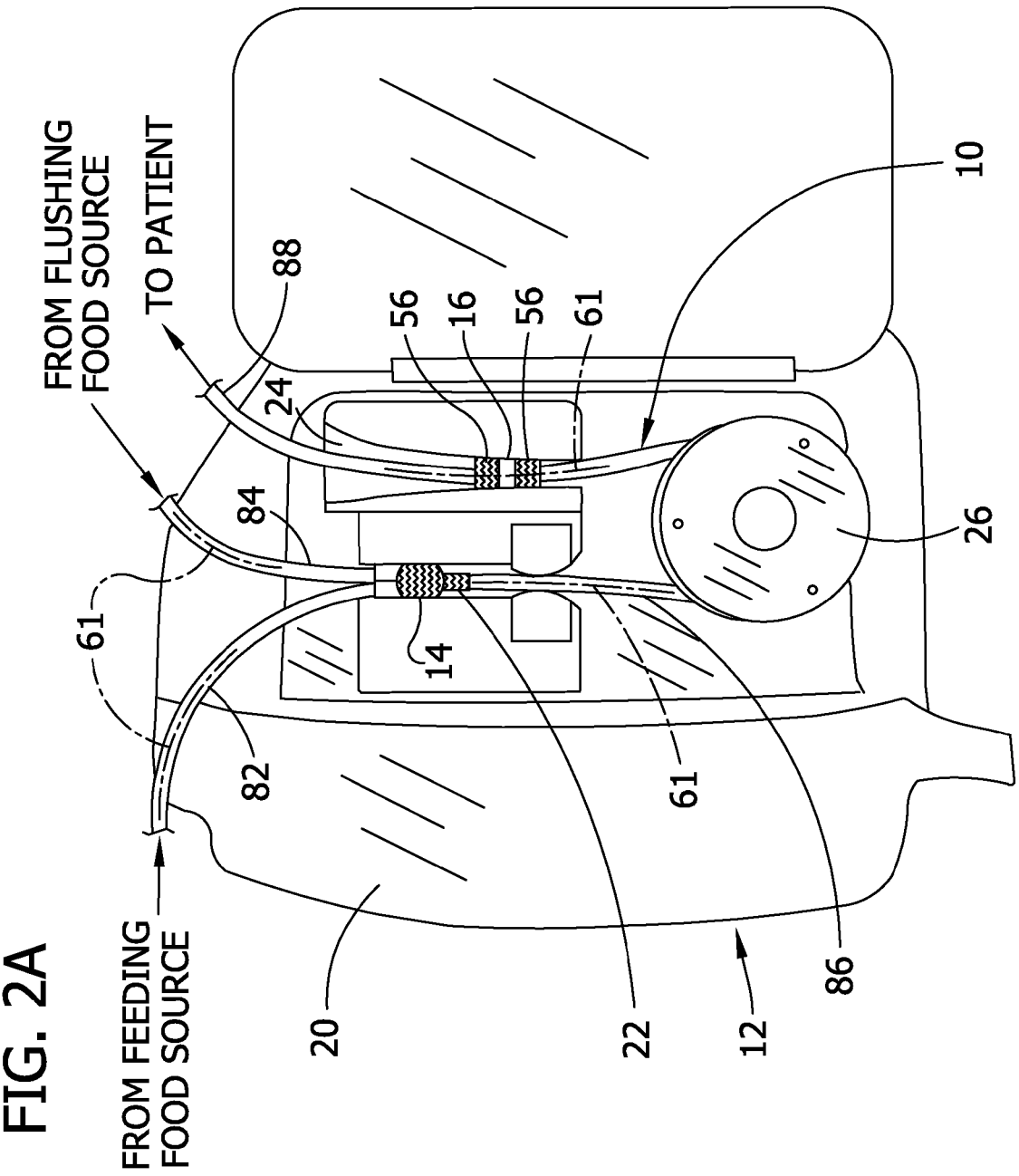

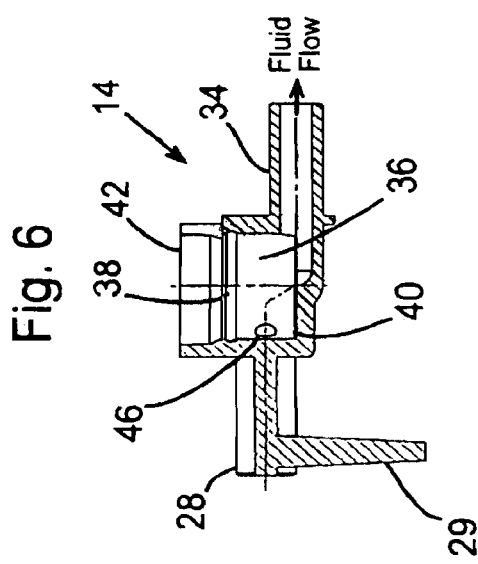
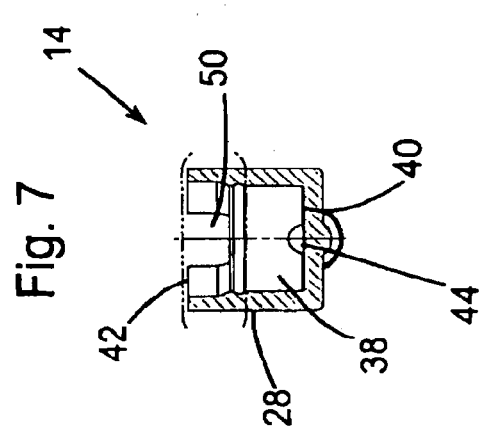
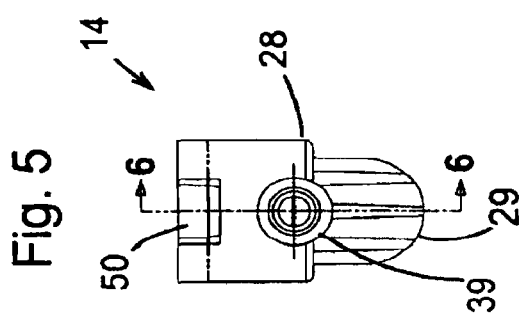
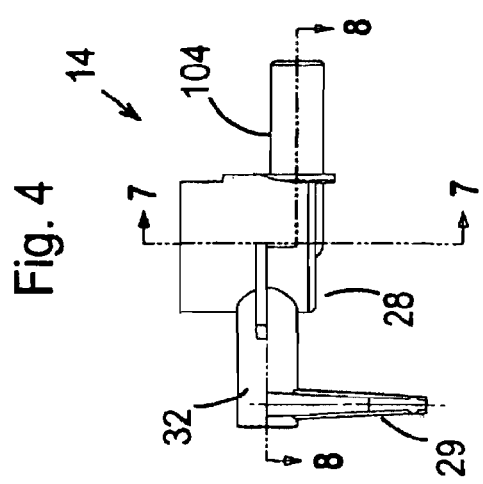

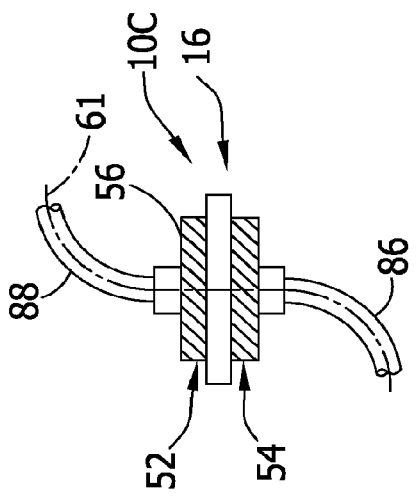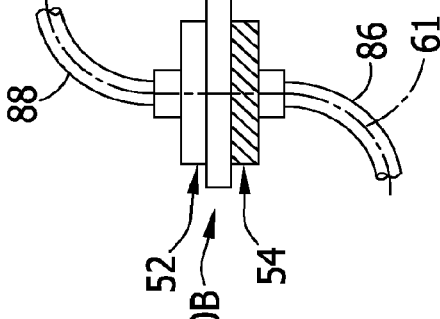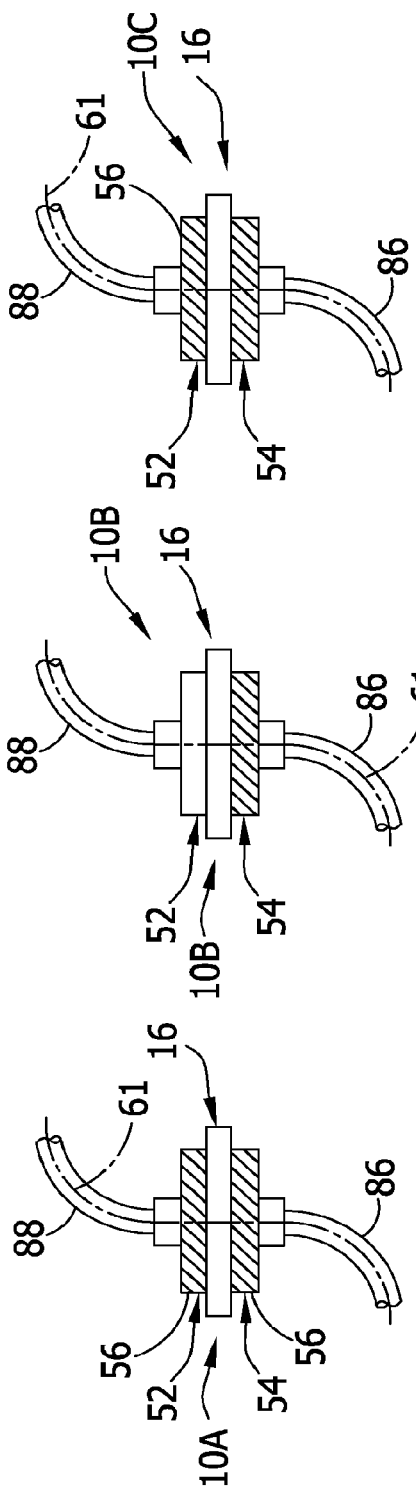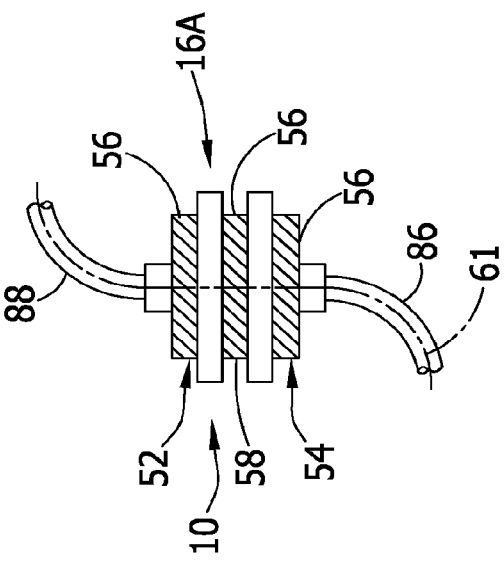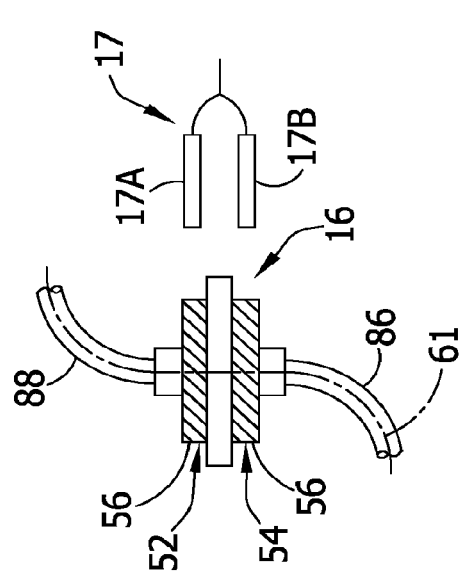

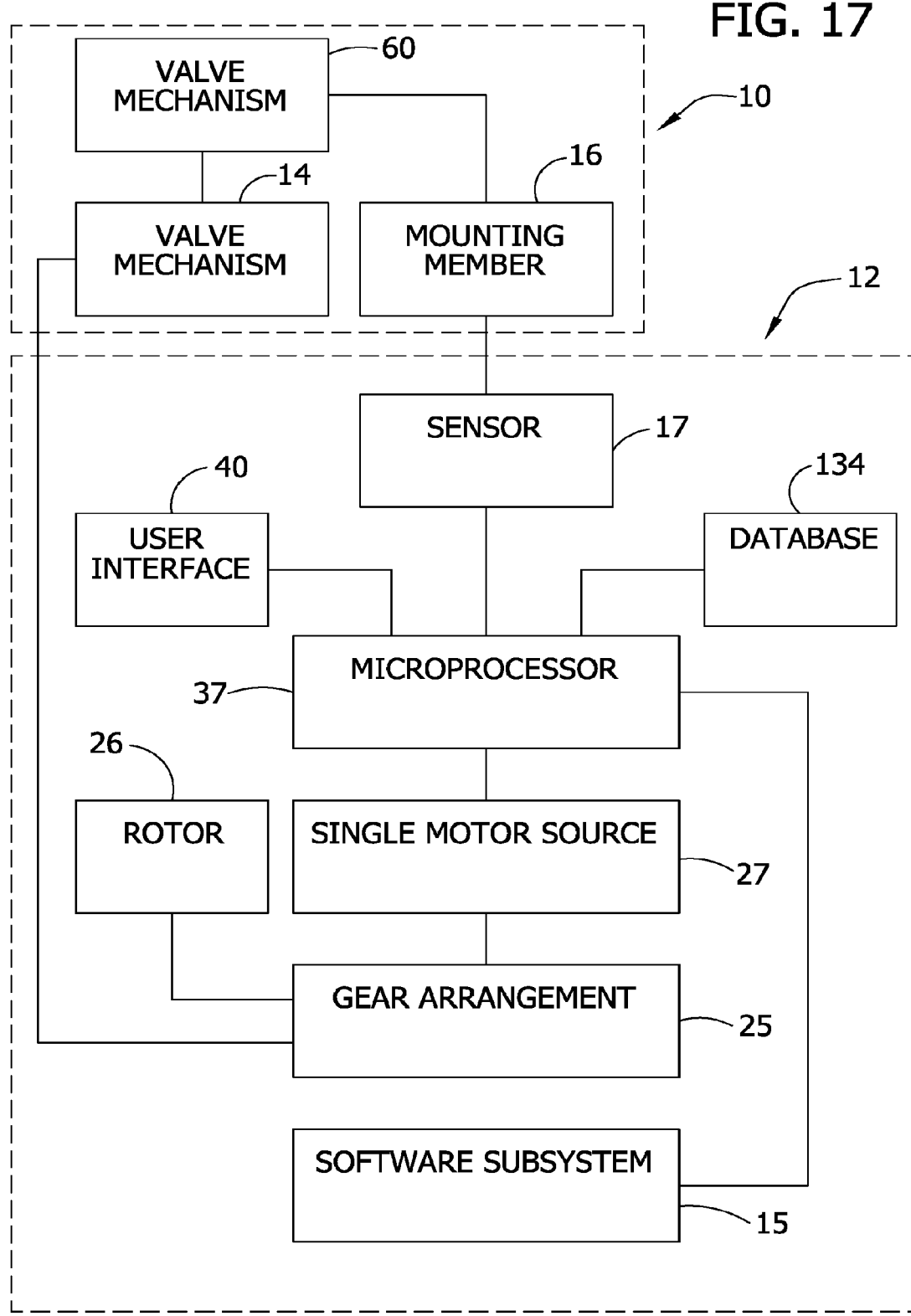

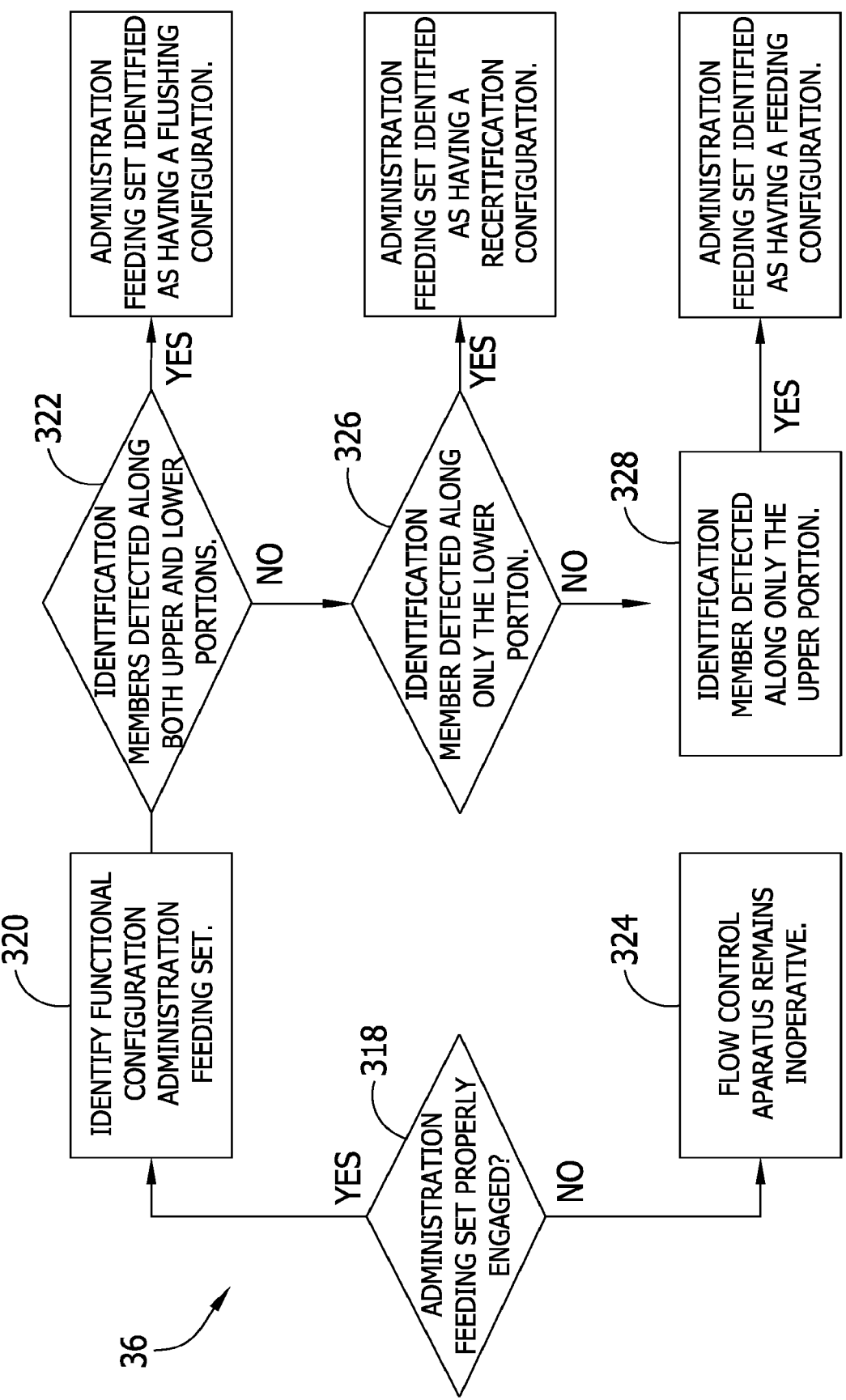

ADMINISTRATION FEEDING SET

CROSS-REFERENCE TO RELATED APPLICATION

This application is a continuation application of and claims the benefit under 35 U.S.C. §120 to U.S. patent application Ser. No. 12/795,889, filed on Jun. 8, 2010, which issued as U.S. Pat. No. 8,034,028, on Oct. 11, 2011, which is a continuation application of U.S. patent application Ser. No. 11/678,350, filed Feb. 23, 2007, which issued as U.S. Pat. No. 7,753,881 on Jul. 13, 2010, which is a divisional application of U.S. patent application Ser. No. 10/853,958, filed on May 25, 2004, which issued as U.S. Pat. No. 7,462,170 on Dec. 9, 2008, the entirety of each of which is hereby incorporated by reference for all purposes.

FIELD OF THE INVENTION

The present invention relates to an administration feeding set adapted to be loaded to a flow control apparatus. The present invention further relates to a valve mechanism adapted to be engaged to a flow control apparatus.

BACKGROUND OF THE INVENTION

Administering fluids containing medicine or nutrition to a patient is well known in the art. Typically, fluid is delivered to the patient by an administration feeding set loaded to a flow control apparatus, such as a peristaltic pump, which delivers fluid to the patient at a controlled rate of delivery. The administration feeding set, when loaded to the flow control apparatus, comprises tubing that delivers fluid from a fluid source to a patient.

A valve mechanism may be located on the tubing for permitting or presenting fluid flow communication through the administration feeding set. Such a valve mechanism may be automatically operated to alternate positions that either prevent or permit fluid flow communication through the tubing when engaged to the flow control apparatus.

Often times it may be difficult to identify administration feeding sets having different functional configurations for performing different kinds of tasks since each type of administration feeding set has a physical appearance that may be indistinguishable from other kinds of administration feeding sets. Accordingly, it is important that the healthcare practitioner be able to readily identify the functional configuration of the administration feeding set being loaded to the flow control apparatus.

Therefore, there is a need for an administration feeding set having a means for identifying the functional configuration of the feeding set and having a valve mechanism that can prevent disengagement of the administration feeding set loaded to the flow control apparatus.

SUMMARY OF THE INVENTION

In one embodiment, an administration feeding set is adapted for use with a flow control apparatus to deliver fluid from at least one fluid source to a patient. The administration feeding set comprises tubing for flow of fluid along a fluid pathway, and a mounting member on the tubing adapted to engage the flow control apparatus. The mounting member has at least two receiving portions co-axial with the fluid pathway. Each receiving portion is adapted to receive an identification member. The administration feeding set also includes one or more identification members selectively positioned on one or more of the at least two co-axial receiving portions of the mounting member to permit identification of the administration feeding set as having a particular functional configuration different from another functional configuration. In one embodiment, an administration feeding set is adapted for use with a flow control apparatus to deliver fluid from at least one fluid source to a patient. The administration feeding set comprises tubing for flow along a fluid pathway, and a mounting member on the tubing receivable in a recess of the flow control apparatus. The mounting member has upper and lower receiving portions co-axial with said fluid pathway. Each receiving portion is adapted to receive an identification member. The administration feeding set also includes one or more upper and lower identification members selectively positioned on one or more of said upper and lower receiving portions of the mounting member. Each identification member comprises a magnetic component on a magnetically-susceptible metallic component. When the administration feeding set is loaded on the flow control apparatus with the mounting member properly positioned in said recess, a sensing device on the flow control apparatus is positioned for detecting any respective upper and lower identification members on the receiving portions of the mounting member to permit identification of the administration feeding set as having a particular functional configuration different from another functional configuration.

BRIEF DESCRIPTION OF THE DRAWINGS

FIG. 2A is a side view of the administration feeding set loaded to a flow control apparatus according to the present invention;

FIG. 4 is a side view of the embodiment of the valve mechanism according to the present invention;

FIG. 5 is an end view of the embodiment of the valve mechanism according to the present invention;

FIG. 6 is a cross-sectional view of the embodiment of the valve mechanism taken along line 6-6 of FIG. 5 according to the present invention;

FIG. 7 is a cross-sectional view of the embodiment of the valve mechanism taken along line 7-7 of FIG. 4 according to the present invention;

FIG. 12 is a diagram of an embodiment of the mounting member with identification members attached to the lower and upper portions thereof according to the present invention;

FIG. 13 is a diagram of an embodiment of the mounting member with an identification member attached only to the lower portion thereof according to the present invention;

FIG. 14 is a diagram of an embodiment of the mounting member with an identification member attached only to the upper portion thereof according to the present invention;

FIG. 15 is a diagram of an embodiment of the mounting member with the identification members attached to the upper and lower portions and further illustrating the related sensor devices according to the present invention;

FIG. 16 is a diagram of an alternative embodiment of a mounting member with identification members attached to upper, middle and lower portions according to the present invention;

FIG. 17 is a simplified block diagram illustrating the various systems related to the administration feeding set loaded to the flow control apparatus according to the present invention; and FIG. 18 is a flow chart of the software subsystem illustrating the process used to detect and identify a functional configuration of an administration feeding set adapted to be loaded to the flow control apparatus according to the present invention.

DESCRIPTION OF THE PREFERRED EMBODIMENTS

Figure 1:
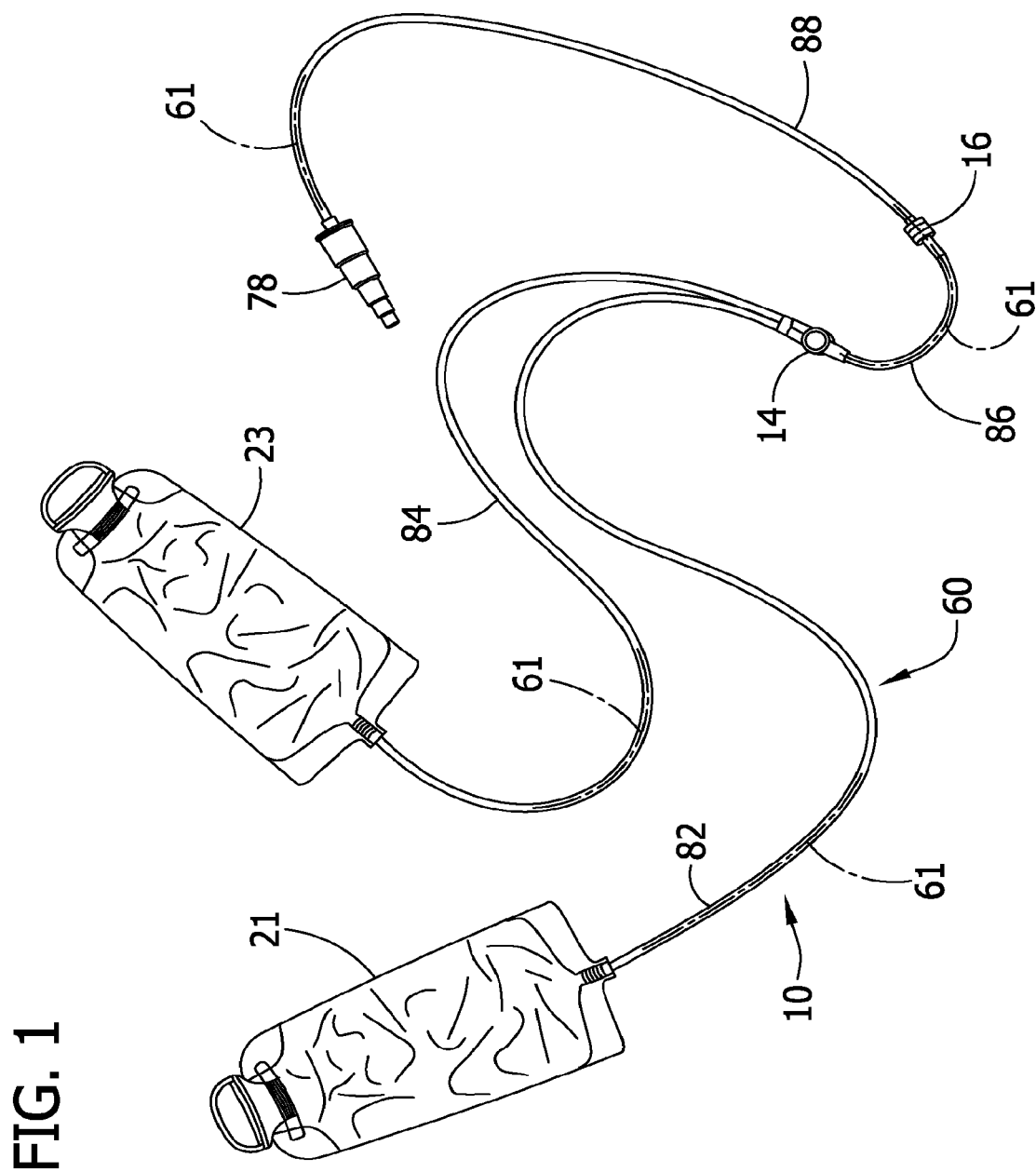
FIG. 1 is a perspective view of an embodiment of the administration feeding set according to the present invention.

Referring to the drawings, an embodiment of the administration feeding set according to the present invention is illustrated and generally indicated as 10 in FIG. 1. This embodiment comprises an administration feeding set 10 adapted to be loaded to a flow control apparatus 12 suitable for delivery of fluid to a patient. In particular, the administration feeding set 10 comprises tubing 60 adapted for fluid flow communication and further adapted to engage the flow control apparatus 12 suitable for driving fluid through the tubing 60. A valve mechanism 14 is in direct communication with the tubing 60 and is adapted to permit or prevent fluid flow communication through the tubing 60 when valve mechanism 14 is engaged to the flow control apparatus 12. In addition, the administration feeding set 10 comprises a mounting member 16 in direct communication with the tubing 60, wherein the mounting member 16 permits identification of the functional configuration of the administration feeding set 10 by the flow control apparatus 12 upon engagement of the mounting member 16 to the flow control apparatus 12. The mounting member 16 also assists in the loading of the administration feeding set 10 to the flow control apparatus 12. As used herein, the term load means that the valve mechanism 14 and mounting member 16 are engaged to flow control apparatus 12 and tubing 60 is placed in a stretched condition between valve mechanism 14 and mounting member 16 such that the administration feeding set 10 is ready for operation with flow control apparatus 12.

In another embodiment, the administration feeding set 10 is identical to the previous embodiment with the exception that the valve mechanism 14 is absent.

In yet another embodiment of the present invention there is provided a novel valve mechanism 14 adapted to be engaged to flow control apparatus 12. The valve mechanism 14 is suitable for permitting or presenting fluid flow communication, as well as preventing disengagement of the valve mechanism 14 from flow control apparatus 12 when the valve mechanism 14 is in a position that permits fluid flow communication.

Administration Feeding Set

As noted above, the administration feeding set 10 comprises tubing 60 that provides a fluid pathway 61 between at least one source of fluid and a patient. Tubing 60 comprises first tubing 86 engaged between the valve mechanism 14 and mounting member 16, and second tubing 88 engaged between mounting member 16 and a connector 78, such as a barbed connector, suitable for attachment to a gastrostomy device attached to a patient. The valve mechanism 14 and mounting member 16 are adapted to engage the tubing 60 to the flow control apparatus 12. As further shown, tubing 60 further comprises third tubing 82 engaged between a feeding fluid source 21 and valve mechanism 14, and fourth tubing 84 engaged between a flushing fluid source 23 and valve mechanism 14, wherein the valve mechanism 14 provides a means for permitting flow of feeding fluid or flushing fluid, or preventing fluid flow communication through tubing 60.

Figure 2B:
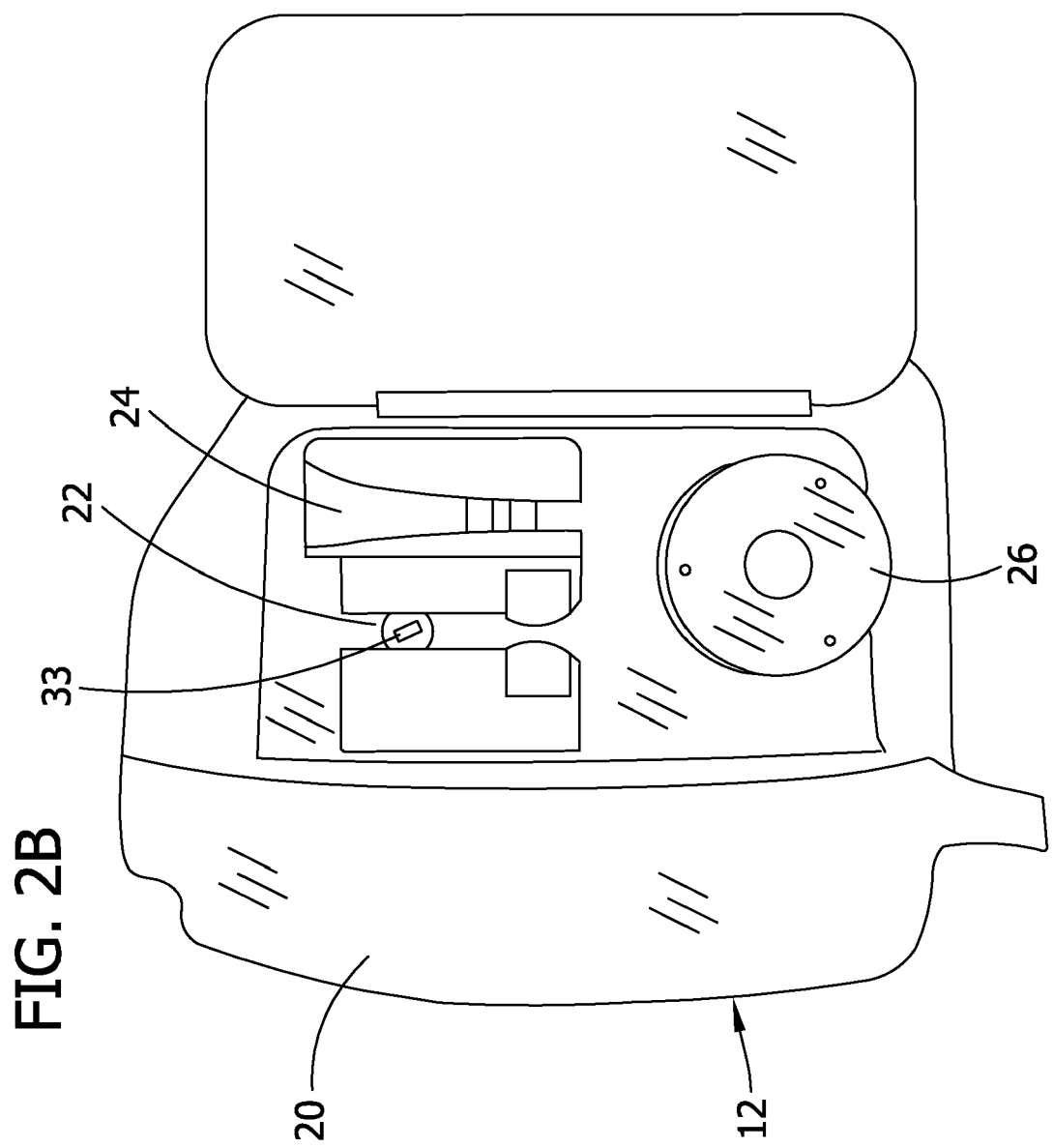
FIG. 2B is a side view of an embodiment of a flow control apparatus prior to loading the administration feeding set thereto according to the present invention.

Referring to FIGS. 2A, 2B and 17 exemplary components and systems of the administration feeding set 10 and flow control apparatus 12 according to an embodiment of the present invention are illustrated. Flow control apparatus 12 comprises a housing 20 that defines first and second recesses 22 and 24 adapted to load the administration feeding set 10 to flow control apparatus 12. A means for driving fluid through tubing 60, such as a rotor 26, is operatively engaged to and through the housing 20 and is adapted to engage tubing 60. Flow control apparatus 12 further includes a sensor 17 ((FIG. 15) that detects the engagement of mounting member 16 to second recess 24 and is in operative communication with a software subsystem 15 as explained in greater detail below. The valve mechanism 14 and rotor 26 are operatively engaged to a gear arrangement 25 driven by a single motor source 27. A suitable flow control apparatus 12 is disclosed in co-pending patent application Ser. No. 10/854,136 (Publication No. 2005/0267439) filed on even date herewith and herein incorporated by reference in its entirety. However, it is understood that any suitable flow control apparatus 12 may be used with administration feeding set 10.

As noted above, administration feeding set 10 comprises tubing 60 engaged to valve mechanism 14 and mounting member 16 adapted for loading the administration feeding set 10 to flow control apparatus 12. Referring specifically to FIGS. 2A and 2B, to load the administration feeding set 10 to the flow control apparatus 12, the valve mechanism 14 is engaged to first recess 22, the first tubing 86 then wrapped around rotor 26, and the mounting member 16 engaged to second recess 24 such that first tubing 86 is placed in a stretched condition around rotor 26 and the administration feeding set 10 is ready for operation with flow control apparatus 12.

As used herein, the portion of tubing 60 leading to the rotor 26 is termed upstream, while the portion of tubing 60 leading away from the rotor 26 is termed downstream. Valve mechanism 14 is engaged to the upstream portion of tubing 60 at first recess 22 and controls the flow of fluid from the respective fluid source through administration feeding set 10, while the mounting member 16 is engaged to the downstream portion of tubing 60 at second recess 24 for loading the administration feeding set 10 to flow control apparatus 12. In an embodiment illustrated in FIG. 1, the feeding fluid source 21 and the flushing fluid source 23 are placed in fluid flow communication with valve mechanism 14 through tubing 60 for permitting or preventing fluid flow from either the feeding or flushing fluid sources 21, 23. However, in another embodiment of the administration feeding set 10, valve mechanism 14 is absent and a means (not shown) for controlling fluid flow through tubing 60 is positioned in an area other than the administration feeding set 10.

Valve Mechanism

The present invention further relates to a valve mechanism 14 that comprises a valve body 28 having at least one inlet 30, 32 in communication with an outlet 34 through a chamber 36 and a valve stem 38 rotatably disposed in the chamber 36. The valve stem 38 has a front portion 40 comprising a fluid pathway 44 defining at least one fluid port 46. This embodiment of valve mechanism 14 is suitable for controlling fluid flow.

In another embodiment, the valve mechanism 14 comprises a valve body 28 having at least one inlet 30, 32 in communication with an outlet 34 through a chamber 36 with the valve body 28 further comprising a slot 50. Valve stem 38 is rotatably disposed in the chamber 36 with the valve stem 38 having a back portion 42 comprising a channel 48. This embodiment of valve mechanism 14 is suitable for preventing disengagement of the valve mechanism 14 from the flow control apparatus 12 when the valve mechanism 14 is in a position that permits fluid flow.

In yet another embodiment, the valve mechanism 14 comprises a valve body 28 having at least one inlet 30, 32 in communication with an outlet 34 through a chamber 36 with the valve body 28 further comprising a slot 50. Valve stem 38 is rotatably disposed in the chamber 36. The valve stem 38 has a front portion 40 comprising a fluid pathway 44 defining at least one fluid port 46 and a back portion 42 comprising a channel 48. This embodiment of valve mechanism 14 is suitable for controlling fluid flow and for preventing disengagement of the valve mechanism 14 from the flow control apparatus 12 when the valve mechanism 14 is in a position that permits fluid flow.

Referring to FIGS. 3-10, valve mechanism 14 is adapted to be engaged to tubing 60 according to the present invention. As noted above, valve mechanism 14 comprises valve body 28 having a first inlet 30 adapted to be in communication with the feeding fluid source 21 through third tubing 82 and a second inlet 32 adapted to be in communication with a flushing fluid source 23 through fourth tubing 84 for providing fluid flow communication with an outlet 34 through chamber 36 interposed between first and second inlets 30, 32 and outlet 34. Valve body 28 further comprises slot 50 along the periphery thereof that is a structural arrangement adapted to receive a rotatable shaft 33 therethrough for operating the valve mechanism 14 as shall be discussed below. Preferably, valve body 28 includes a tab 29 that enables the user to easily engage valve mechanism 14 to flow control apparatus 10.

As noted above, valve stem 38 has front portion 40 comprising a fluid pathway 44 that defines at least one fluid port 46 to establish fluid flow through valve body 28. Fluid flow is established when valve stem 38 is rotated such that any one fluid port 46 is aligned with either the first or second inlets 30 and 32, thereby establishing fluid flow communication between first or second inlets 30, 32 and outlet 34.

Referring to FIGS. 2B, 3A-C, 6, and 17, channel 48 has opposed openings 48A and 48B adapted to engage rotatable shaft 33 when engaging the valve mechanism 14 to the first recess 22 of flow control apparatus 12. As shown, flow control apparatus 12 further comprises a gear arrangement 25 operatively engaged to rotatable shaft 33 that is driven by the single motor source 27. The engagement between the valve mechanism 14 and the rotatable shaft 33 is accomplished by rotating the valve stem 38 and orienting channel 48 such that one of the openings 48A or 48B is aligned with slot 50 that permits the shaft 33 to be inserted into the interior portion of channel 48. Channel 48 provides a means for preventing disengagement of valve mechanism 14 from flow control apparatus 12 when the channel 48 is rotated to an orientation that misaligns the channel 48 with slot 50 and places the valve mechanism 14 in a position that permits fluid flow communication through tubing 60.

Conversely, the valve mechanism 14 permits disengagement from the flow control apparatus 12 when the channel 48 is rotated to an orientation that aligns one of the opposed openings 48A or 48B with slot 50 and places the valve mechanism 14 in a position that prevents fluid flow communication through tubing 60. More particularly, valve mechanism 14 must be placed in a blocking position that rotates valve stem 38 such that fluid ports 46 are in misalignment with both the first and second inlets 30, 32 to prevent fluid flow communication in order to disengage valve mechanism 14 from housing 20. Then the flow control apparatus 12 directs rotatable shaft 33 through gear arrangement 25 to rotate valve stem 38 such that the valve mechanism 14 is placed in a blocking position shown in FIG. 10 C, channel 48 is aligned with slot 50 while shaft 33 is disengaged through slot 50.

According to one aspect of the present invention, valve mechanism 14 is configured to prevent manual operation thereof by a user such that valve mechanism 14 can be operated only when engaged to the flow control apparatus 12. Specifically, valve stem 38 must be engaged to shaft 33 in order to permit operation of the flow control apparatus 12, thereby making valve mechanism 14 difficult to operate manually and particularly useful as a tamper-proof device.

Figure 3A:
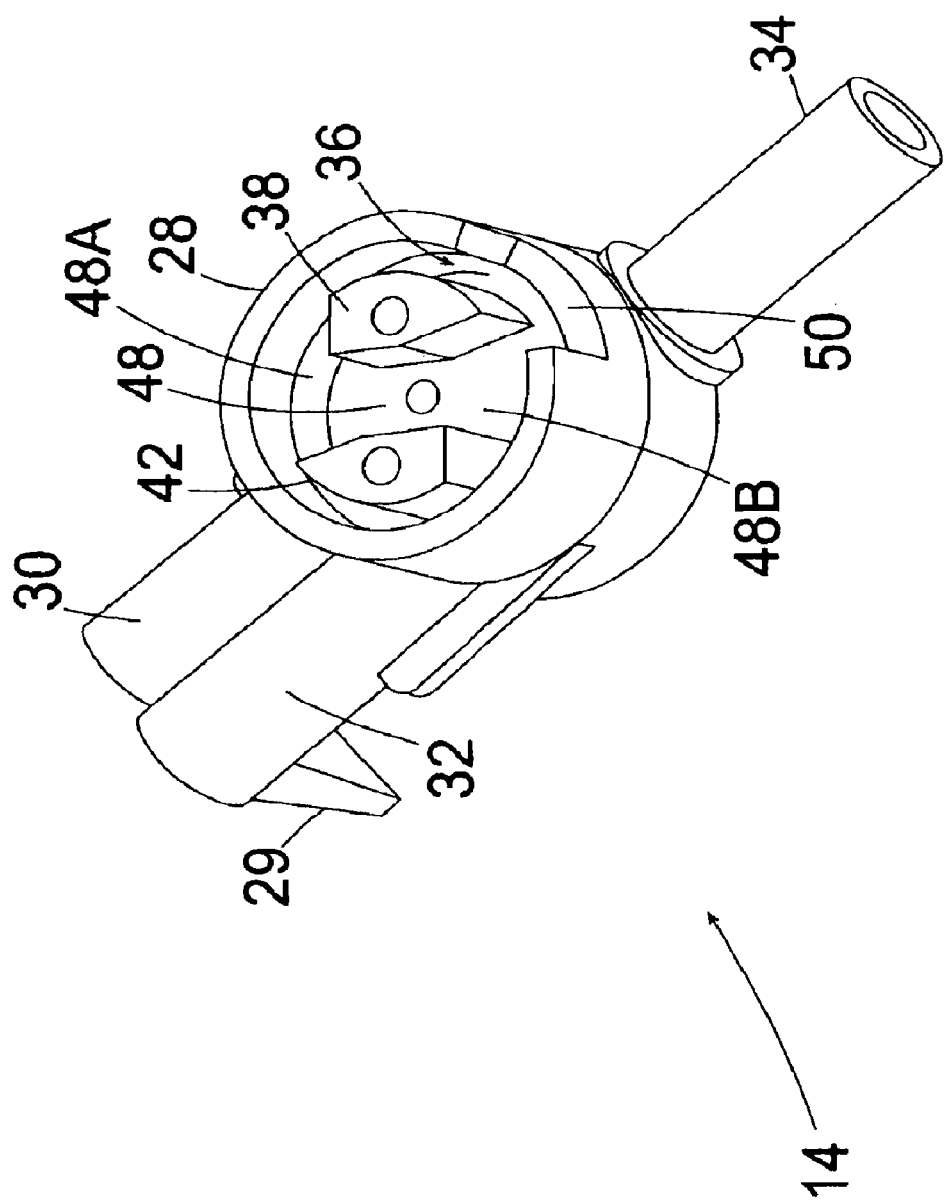
FIG. 3A is a partial perspective view of an embodiment of the valve mechanism shown in the feeding position according to the present invention.
Figure 3B:
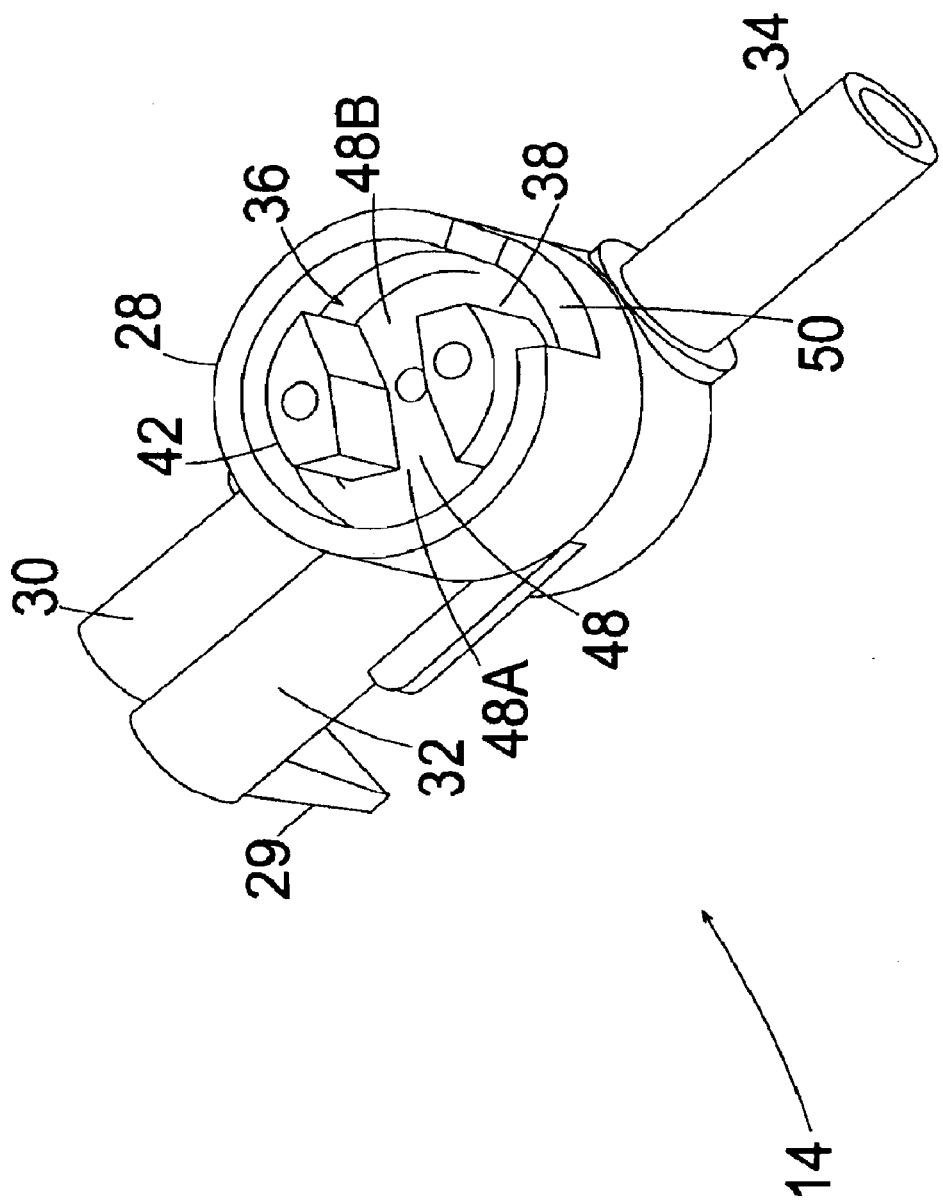
FIG. 3B is a partial perspective view of the embodiment of the valve mechanism shown in the flushing position according to the present invention.
Figure 3C:
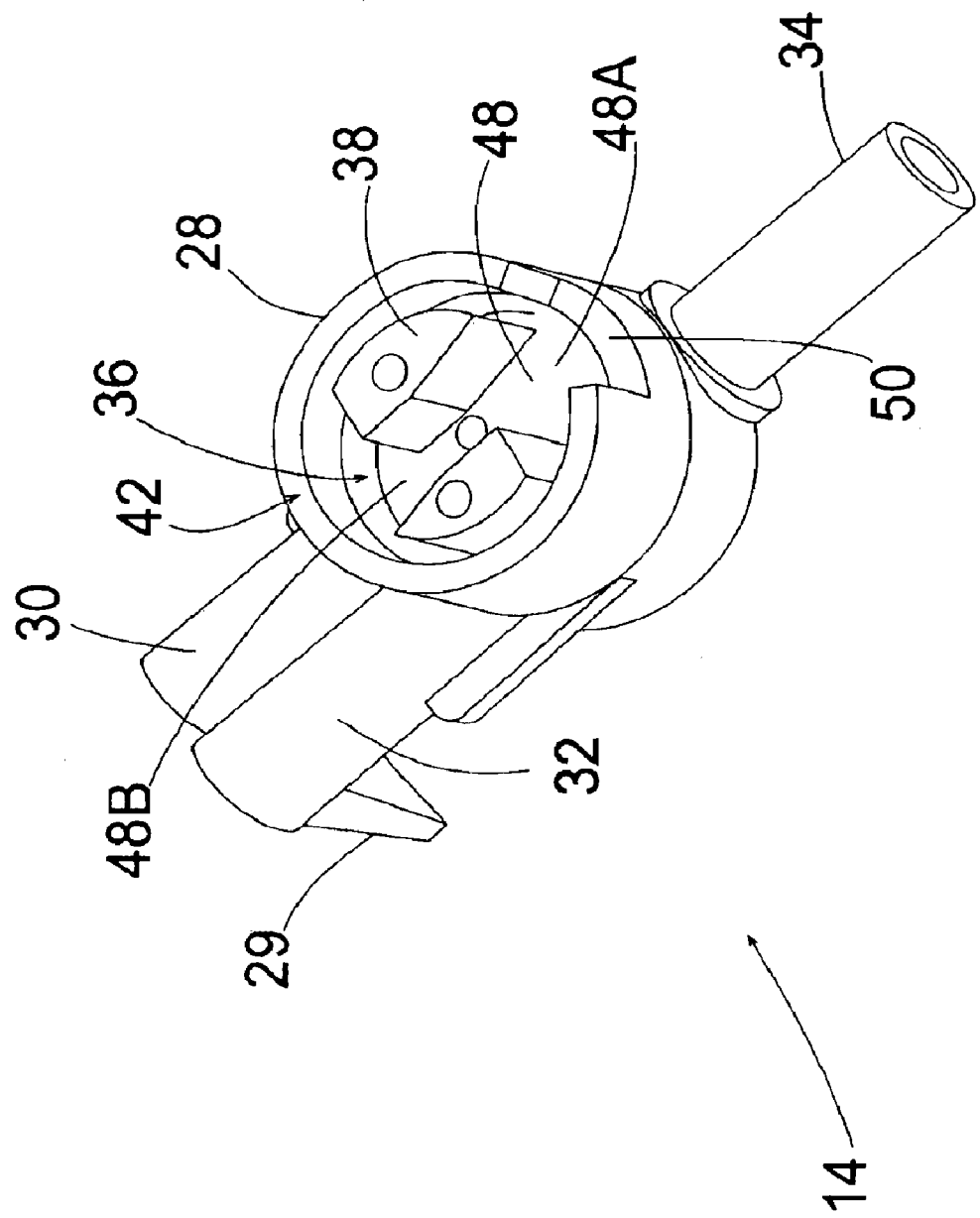
FIG. 3C is a perspective view of the embodiment of the valve mechanism shown in the blocking position according to the present invention.
Figure 10:
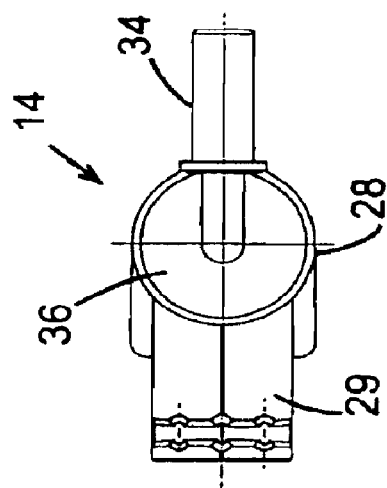
FIG. 10 is a bottom view of the embodiment of the valve mechanism according to the present invention.
Figure 9:
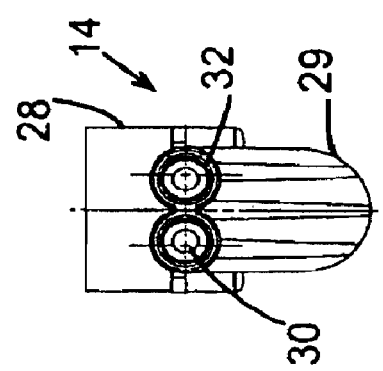
FIG. 9 is an opposing end view of the embodiment of the valve mechanism according to the present invention.
Figure 8:
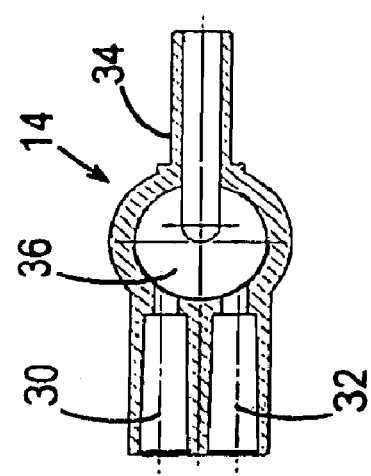
FIG. 8 is a cross-sectional view of the embodiment of the valve mechanism taken along line 8-8 of FIG. 4 according to the present invention.

In operation, the rotation of valve stem 38 by the rotatable shaft 33 when driven by single motor source 27 prevents or permits fluid flow communication through administration feeding set 10 by valve mechanism 14. Flow control apparatus 12 further includes a microprocessor 37 that controls the rotation of valve stem 38 so that either first inlet 30 or second inlet 32 is in alignment or misalignment with the fluid ports 46 when permitting or preventing fluid flow communication. When any one of the fluid ports 46 is aligned with either of the first or second inlets 30, 32 fluid is permitted to flow into fluid port 46, through fluid pathway 44 and then exit out from outlet 34 as illustrated in FIGS. 3A, 3B and 6. Valve stem 38 is rotated in only direction, for example counter-clockwise, such that the valve stem 38 rotates the fluid pathway 44 in one direction only when aligning or misaligning any one of the fluid ports 46 with either first or second inlets 30, 32, thereby permitting a one-way, multiple engagement operation between the fluid ports 46 and first and second inlets 30, 32 that either permits or prevents fluid flow communication. Referring specifically to FIG. 6, when valve stem 38 aligns any one of fluid ports 46 with either first or second inlets 30, 32, fluid flow communication is established between either first or second inlets 30, 32 and outlet 34.

Based on the foregoing, when any one of the fluid ports 46 of valve stem 38 is aligned with any one of the first or second inlets 30, 32 to permit fluid flow communication the channel 48 is misaligned with slot 50, thereby preventing disengagement of the valve mechanism 14 from the flow control apparatus 12. When the fluid ports 46 are misaligned with the first and second inlets 30, 32 to prevent fluid flow communication the channel 48 is aligned with slot 50, thereby permitting disengagement of the valve mechanism 14 from flow control apparatus 12.

Figure 11A:
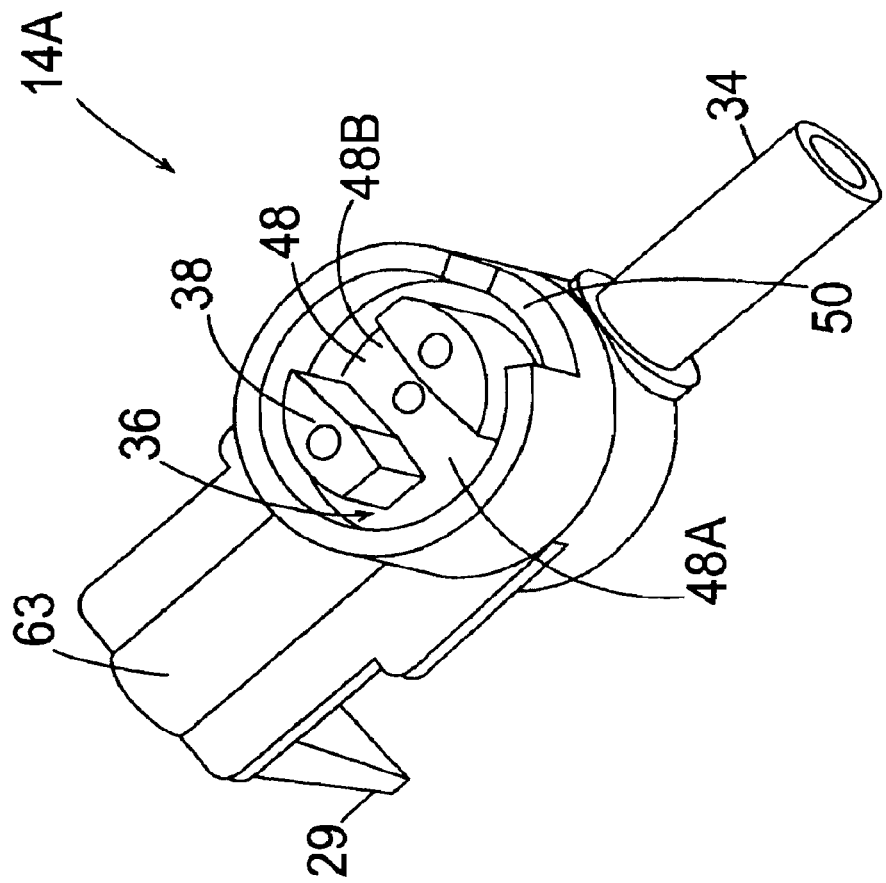
FIG. 11A is a perspective view of an alternative embodiment of the valve mechanism shown in the feeding position according to the present invention.
Figure 11B:
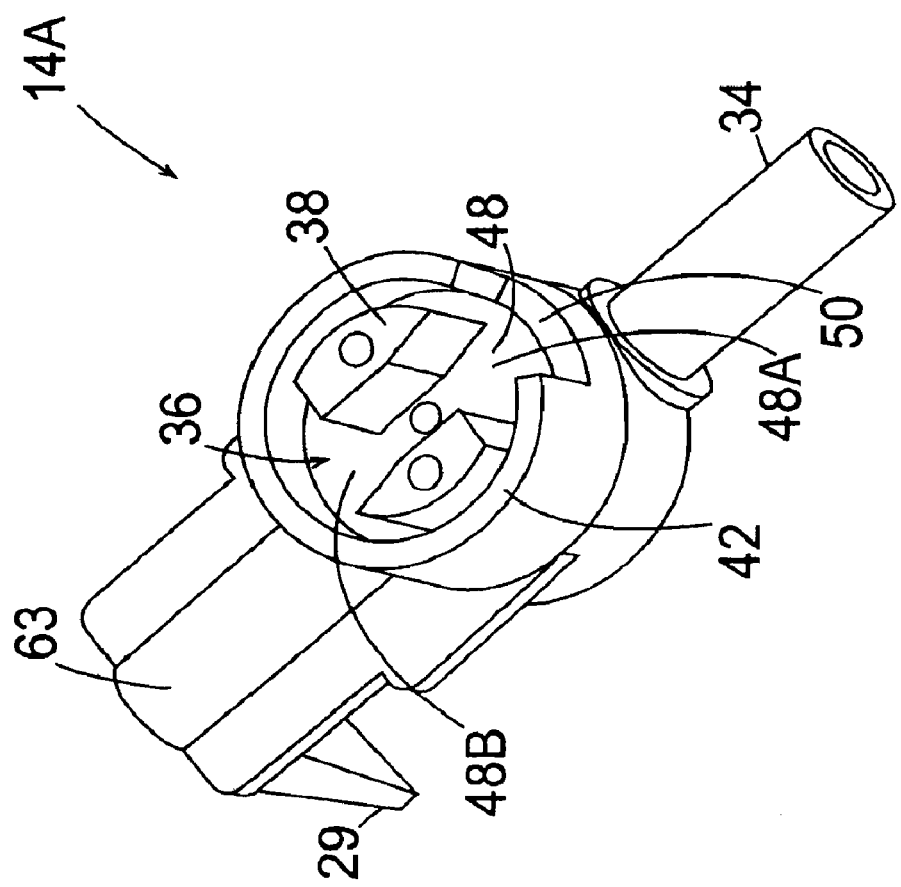
FIG. 11B is a perspective view of the alternative embodiment of the valve mechanism shown in the blocking position according to the present invention.

Referring to FIGS. 11A and 11B, an alternative embodiment of the valve mechanism designated 14A is illustrated according to the present invention. Valve mechanism 14A is similar in structure and operation to the preferred embodiment of valve mechanism 14, except there is only a single feeding inlet 63 for providing feeding fluid through the administration feeding set 10 from the feeding fluid source 21, rather than first and second inlets 30, 32 which permit both feeding and flushing functions. Accordingly, valve mechanism 14A alternates between a feeding position (FIG. 11A) for providing fluid to a patient and a blocking position (FIG. 11B) that prevents fluid flow communication.

Administration Feeding Set Identifier System

According to another aspect of the present invention, mounting member 16 assists in loading the administration feeding set 10 to the flow control apparatus 12 and is in operative communication with software subsystem 15 when engaged to second recess 24 which provides a means for identifying the type of administration feeding set 10. As shown in FIGS. 2A, and 12-17, mounting member 16 has an upper receiving portion 52 and a lower receiving portion 54 each co-axial with the fluid pathway 61 and each adapted to receive an identification member 56 when attached thereto. Preferably, mounting member 16 has a cylindrical shape that concentrically surrounds tubing 60 and surrounds the fluid pathway 61 extending through the mounting member from one end to its opposite end. The mounting member 16 is configured to be engaged to second recess 24 when loading administration feeding set 10 to flow control apparatus 12 such that sensor 17 detects the presence of one or more identification members 56 attached to mounting member 16. Sensor 17 is preferably a Hall-effect sensor or other type of proximity sensor that is positioned near the second recess 24 such that sensor 17 can detect the presence of one or more identification members 56 when the mounting member 16 is engaged to second recess 24.

When mounting member 16 is engaged to second recess 24, the attachment of one or more identification members 56 to mounting member 16 provides a means for allowing software subsystem 15 to identify the functional configuration of the administration feeding set 10 loaded to flow control apparatus 12 and detected by sensor 17. Specifically, as shown in FIG. 12, mounting member 16 has at least one or more identification members 56 attached thereto in accordance with an identification scheme that permits software subsystem 15 to identify the functional configuration of the administration feeding set 10 loaded to flow control apparatus 12. Preferably, identification members 56 attached thereto in accordance with an identification scheme that permits software subsystem 15 to identify the functional configuration of the administration feeding set 10 loaded to flow control apparatus 12. Preferably, identification members 56 are magnetic components or, in the alternative, magnetically-susceptible metallic components capable of detection by sensor 17 without requiring direct physical contact with sensor 17. In order to identify the functional configuration of the administration feeding set 10 loaded to flow control apparatus 12 microprocessor 37 is operatively associated with a database 134 containing one or more identification schemes for identifying different functional configurations for an administration feeding set 10.

According to another aspect of the present invention, an identification member 56 may be attached to the upper portion 52, lower portion 54, or both portions 52 and 54 of mounting member 16. The attachment of at least one identification member 56 to the mounting member 16 will vary to correspond with the number of different functional configurations. Each different functional configuration for an administration feeding set 10 will have a predetermined number and location of identification member(s) 56 attached to mounting member 16 that identifies the administration feeding set 10, such as feeding, flushing or re-certification, when mounting member 16 is detected by the sensor 17 and this data is communicated to the software subsystem 15 through microprocessor 37.

The recognition of the different number and attachment of identification members 56 to mounting member 16 and the identification of the type of functional configuration of administration feeding set 10 loaded to flow control apparatus 12 is based on a two-step process. First, sensor 17 detects the location and number of identification member(s) 56 when mounting member 16 is engaged to second recess 24; and second, software subsystem 15 that is in operative communication with sensor 17 determines the functional configuration of the loaded administration feeding set 10 based on the location and number of identification members 56 detected on mounting member 16 as shall be explained in greater detail below.

Referring to FIG. 15, sensor 17, for use with an embodiment of the software subsystem 15, comprises a pair of sensor devices 17A and 17B that detect the location and number of one or more identification members 56 attached to mounting member 16. Sensor 17 can be any known type of proximity sensor for detecting an identification member 56, preferably a magnetic component, or in the alternative a magnetically-susceptible metallic component, attached to mounting member 16. In addition, sensor 17 may also comprise any number of sensor devices with each sensor device corresponding to a portion of the mounting member 16 for detecting the presence of an identification member 56. In one embodiment, a pair of magnetic field proximity sensors or magnetic switch-type sensors may be provided, although the present invention contemplates that other types of sensors may be used, such as various inductive coil arrangements. Sensor 17 is positioned near to second recess 24 such that each sensor device 17A and 17B is positioned relative to a corresponding portion in close proximity with mounting member 16 when administration feeding set 10 is loaded to flow control apparatus 12. Upon engagement of mounting member 16, sensor 17A and sensor 17B are capable of detecting the presence of an identification member 56 attached to the corresponding upper and lower portions 52 and 54 of mounting member 16.

In particular, sensor devices 17A and 17B are positioned near the second recess 24 in proximity to the upper and lower portions 52 and 54 of the mounting member 16 and are capable of detecting a corresponding identification member 56 attached to portions 52 and 54, respectively. Accordingly, sensor device 17A is placed in a position to detect an identification member 56 attached only to upper portion 52 of mounting member 16, while sensor device 17B is positioned to detect the presence of an identification member 56 attached only to the lower portion 54 of mounting member 16. As noted above, the present invention contemplates that a corresponding sensor device 17 is provided for each additional portion of mounting member 16 adapted to receive an identification member 56.

As further noted above, software subsystem 15 provides a means for allowing the flow control apparatus 12 to identify the functional configuration of administration feeding set 10 loaded to flow control apparatus 12. FIG. 18 illustrates the sequence of steps software subsystem 15 executes through microprocessor 37 to identify a functional configuration of administration feeding set 10 loaded to flow control apparatus 12 from a plurality of functional configurations. At decision point 318, software subsystem 15 determines whether or not an administration feeding set 10 is loaded to flow control apparatus 12. If the administration feeding set 10 is not loaded, then at step 324 the flow control apparatus 12 remains inoperative. However, if the administration feeding set 10 is loaded to flow control apparatus 12, the administration feeding set 10 and flow control apparatus are ready for operation once software subsystem 15 then identifies the functional configuration of administration feeding set 10 being loaded to flow control apparatus 12.

When engagement of mounting member 16 is detected at decision point 318, microprocessor 37 directs the flow control apparatus 12 to display an indication of such engagement to the user. At step 320, software subsystem 15 determines what functional configuration of administration feeding set 10 is loaded to the flow control apparatus 12 and ready for operation.

In order to identify the functional configuration of administration feeding set 10, software subsystem 15 executes a series of decision points 322, 326, and 328. At each of these decision points software subsystem 15 compares the number and placement of identification member 56 detected by sensor 17 with data stored in database 134.

At decision point 322, if sensor 17 detects an identification member 56 attached to both the upper and lower portions 52, 54 of mounting member 16, software subsystem 15 identifies the administration feeding set 10 as having a flushing configuration. However, if an identification member 56 is not detected at both the upper and lower portions 52, 54 then software subsystem 15 proceeds to decision point 326. At decision point 326, if sensor 17 detects an identification member 56 attached to only lower portion 54 information retrieved from database 134 identifies the administration feeding set 10 as having a re-certification configuration. However, if sensor 17 detects an identification member 56 attached only to the upper portion 52 of mounting member 16 at step 328, then software subsystem 15 determines that the administration feeding set 10 loaded to flow control apparatus 12 has a feeding configuration.

Once software subsystem 15 identifies the functional configuration of administration feeding set 120 loaded to flow control apparatus 12, microprocessor 37 directs that this information be displayed on user interface 40. Thus, software subsystem 15 is able to not only detect that the administration feeding set 10 is loaded, but also determine and display the functional configuration of the administration feeding set 10, such as feeding, flushing or re-certification loaded to the flow control apparatus 12. However, the present invention contemplates that alternate arrangements for placement of an identification member 56 attached to upper and lower portions 52, 54 may correspond to different functional configurations for administration feeding set 10.

In an alternative identification scheme shown in FIG. 16, an identification member 56 may be attached to three different portions of a mounting member 16A, which increases the total number of functional configurations capable of being detected by the sensor 17 from three to seven configurations. The present invention further contemplates that increasing the number of portions on mounting member 16A for engaging an identification member 56 increases the number of different functional configurations for administration feeding set 10 that can be detected and identified by flow control apparatus 12. Preferably, the software subsystem 15 utilizes the following equation to determine the number of functional configurations for mounting member 16:

$$X = 2^n - 1$$

Wherein X is the number of potential different functional configurations and n is the number of receiving portions along mounting member 16.

Preferably, mounting member 16A may be a concentric sleeve having at least three separate receiving portions co-axial with the fluid pathway 61, and with each portion adapted to receive an identification member 56 according to one or more identification schemes. In this alternative embodiment, mounting member 16A preferably has a middle receiving portion 58 in additional to the upper and lower portions 52, 54 that are each adapted to receive an identification member 56. Additionally, to further increase the number of possible identification schemes the polarity on any number of identification members 56 may be reversed using techniques known in the art in order to provide another means of detecting one or more identification members 56 attached to mounting member 16.

It should be understood from the foregoing that, while particular embodiments of the invention have been illustrated and described, various modifications can be made thereto without departing from the spirit and scope of the invention as will be apparent to those skilled in the art.

What is claimed is:

1. An administration feeding set for use with a flow control apparatus to deliver fluid from at least one fluid source to a patient, the flow control apparatus comprising a recess, a sensing device disposed proximate to the recess for detecting magnetic components or magnetically-susceptible metallic components, and a microprocessor operatively associated with a software subsystem, the administration feeding set comprising:
   a tubing for flow of fluid along a fluid pathway;
   a mounting member on the tubing receivable in the recess of said flow control apparatus, said mounting member having upper and lower receiving portions co-axial with said fluid pathway, each receiving portion being adapted to receive an identification member; and
   one or more upper and lower identification members selectively positioned on one or more of said upper and lower receiving portions of the mounting member, each identification member comprising a magnetic component or a magnetically-susceptible metallic component;
   the arrangement being such that when the administration set is loaded on the flow control apparatus with the mounting member properly positioned in said recess, the sensing device is positioned for detecting any respective upper and lower identification members on the receiving portions of the mounting member to permit identification of the administration feeding set as having a particular functional configuration different from another functional configuration, wherein said particular functional configuration comprises one of a feeding configuration, a flushing configuration and a re-certification configuration and said another functional configuration comprises another of a feeding configuration, a flushing configuration and a re-certification configuration.

2. The administration feeding set as set forth in claim 1 wherein a first identification member is mounted on one of said receiving portions and a second identification member is mounted on another of said receiving portions.

3. The administration feeding set as set forth in claim 1 wherein the identification members can be arranged to indicate up to three separate functional configurations.

4. The administration feeding set as set forth in claim 1 wherein the identification members can be arranged to indicate up to seven separate functional configurations.

5. The administration feeding set as set forth in claim 1 wherein said fluid pathway extends through the mounting member from one end of the mounting member to an opposite end of the mounting member.

6. The administration feeding set as set forth in claim 5 wherein said tubing comprises a first tubing connected to a first of said receiving portions and a second tubing connected to a second of said receiving portions.

7. The administration feeding set as set forth in claim 1 wherein said fluid pathway extends through the mounting member, and wherein each of said at least two receiving portions of the mounting member surrounds said fluid pathway.

8. The administration feeding set as set forth in claim 7 wherein said tubing comprises a first tubing connected to a first of said receiving portions and a second tubing connected to a second of said receiving portions.

9. The administration feeding set as set forth in claim 8 wherein said first tubing is stretchable and adapted to stretch when the administration feeding set is installed on said flow control apparatus.

10. The administration feeding set as set forth in claim 1 wherein said mounting member comprises at least three co-axial receiving portions each adapted to receive an identification member.

11. The administration feeding set as set forth in claim 10 wherein a first identification member is mounted on a first of said receiving portions, a second identification member is mounted on a second of said receiving portions, and a third identification member is mounted on a third of said receiving portions.

12. The administration feeding set as set forth in claim 1 wherein the administration set further comprises a valve mechanism upstream from said mounting member for control of fluid flow through said tubing, the valve mechanism being adapted to engage said flow control apparatus, and wherein said valve mechanism is movable between at least two positions including an open position permitting fluid flow and a closed position preventing fluid flow, and wherein the valve mechanism is configured such that the valve mechanism can be disengaged from the flow control apparatus when in said closed position but cannot be disengaged from the flow control apparatus when in said open position.

13. The administration feeding set as set forth in claim 1 wherein a polarity of at least one of said upper and lower identification members is reversed to provide an additional means for indicating a particular functional configuration.

14. The administration feeding set as set forth in claim 1 wherein said particular functional configuration is a feeding configuration and said another functional configuration is one of a flushing configuration and a re-certification configuration.

15. The administration feeding set as set forth in claim 1 wherein said particular functional configuration is a flushing configuration and said another functional configuration is one of a feeding configuration and a re-certification configuration.

16. The administration feeding set as set forth in claim 1 wherein said particular functional configuration is a re-certification configuration and said another functional configuration is one of a flushing configuration and a feeding configuration.

* * * * *